(12) United States Patent
Lerner et al.

(10) Patent No.: US 6,740,042 B1
(45) Date of Patent: May 25, 2004

(54) BILATERAL SIMULTANEOUS DOPPLER MEASUREMENT OF SEGMENTED SPHYGMOMANOMETRY

(75) Inventors: David A. Lerner, St. Paul, MN (US); William Lee Rogers, Oakdale, MN (US)

(73) Assignee: Biomedix, Inc., Vadnais Heights, MN (US)

(*) Notice: Subject to any disclaimer, the term of this patent is extended or adjusted under 35 U.S.C. 154(b) by 0 days.

(21) Appl. No.: 10/236,067

(22) Filed: Sep. 5, 2002

Related U.S. Application Data
(60) Provisional application No. 60/317,282, filed on Sep. 5, 2001.

(51) Int. Cl.[7] .................................................. A61B 8/06
(52) U.S. Cl. ........................................................ 600/453
(58) Field of Search ................................. 600/407, 437, 600/438, 440, 441, 442, 443, 446, 447, 448, 449, 450–471, 485, 487, 490, 492, 493, 497, 500, 504, 508–520

(56) References Cited

U.S. PATENT DOCUMENTS

| | | | |
|---|---|---|---|
| 4,154,238 A | * 5/1979 | Link | 600/494 |
| 5,503,156 A | * 4/1996 | Millar | 600/485 |
| 5,634,467 A | * 6/1997 | Nevo | 600/490 |

* cited by examiner

Primary Examiner—Ali Imam
(74) Attorney, Agent, or Firm—Faegre & Benson LLP (57) ABSTRACT

A system and method for simultaneous, bilateral, segmental blood pressure measurement are disclosed. In one illustrative embodiment of the invention, two Doppler modules are configured to operate at nominally the same Doppler carrier frequency so that they probe for substantially the same range of physiological information. However, the Doppler carrier frequencies for the Doppler modules are also sufficiently different to substantially avoid interference between the two modules. A phase-locked loop (PLL) used to demodulate the velocity signals in each Doppler module efficiently blocks interference signals because they have frequencies that are the difference in the Doppler carrier frequencies and that are outside the locking range of the PLL. Broad-band RF amplifiers and Doppler transducers are used to ensure that the frequency responses of the Doppler modules are substantially the same.

24 Claims, 9 Drawing Sheets

$$\frac{V_Q}{\emptyset in} = \frac{KF(s)}{1+K_oKF(s)/s} = \frac{SKF(s)}{S+K_oKF(s)}$$

$\omega in$ = Input Signal Frequency $\quad \omega in = \frac{d\emptyset in}{dt} \longrightarrow \omega in = S\emptyset in(s)$
$\emptyset in$ = Input Signal Phase $$\frac{V_o}{\omega in} = \frac{KF(s)}{S+K_oKF(s)}$$

if $F(s) = \frac{S}{S+\omega_F} \quad$ (1st order low pass filter)

$$\boxed{\frac{V_o}{\omega in} = \frac{1}{K_o}\left[\frac{1}{1+\frac{S}{K_oK}+\frac{S^2}{\omega_F K_oK}}\right]}$$

BILATERAL SIMULTANEOUS DOPPLER MEASUREMENT OF SEGMENTED SPHYGMOMANOMETRY

CROSS REFERENCE TO RELATED APPLICATION

The present application claims priority to U.S. Provisional Application No. 60/317,282, entitled "BILATERAL SIMULTANEOUS DOPPLER MEASUREMENT OF SEGMENTED SPHYGMOMANOMETRY" and filed Sep. 5, 2001. Said Provisional Application is incorporated herein by reference.

FIELD OF THE INVENTION

The invention relates generally to blood pressure measurement. More particularly, the invention relates to a method and system for simultaneous, bilateral, segmental measurement of blood pressure using Doppler techniques.

BACKGROUND OF THE INVENTION

Segmental blood pressure is one of the most important parameters to measure in understanding and diagnosing vascular diseases. Blood pressure measurement (sphygmomanometry) for segmental systolic pressures using Doppler techniques has gained wide acceptance, and is the modality of choice in many incidences. This is in large part because of Doppler's greater sensitivity and accuracy when compared with photoplethysmographic and oscillometric methods and the Doppler method's lesser sensitivity to temperature fluctuations. The Doppler-based systems also have the desirable characteristic of being vessel-specific.

One application of Doppler sphygmomanometry is in segmental blood pressure measurements, i.e., tracking blood pressures at different parts of the body. For example, because of its vessel-specificity, Doppler sphygmomanometry can be used to trace blood pressures along an artery in limbs for diagnosis of peripheral arterial disease (PAD).

In performing segmented blood pressure measurements, it is often desirable to conduct bilateral measurements, i.e., measurements at symmetrically paired locations, such as left and right feet, and left and right forearms. The comparison between blood pressures at symmetrical locations may yield clues to the condition of blood vessels on either side. The ideal time for making such comparisons would be when the blood pressures at both locations are measured for the same heartbeat so that any differences between the measurements are not attributable to the difference in the different heartbeats.

Figure 9:
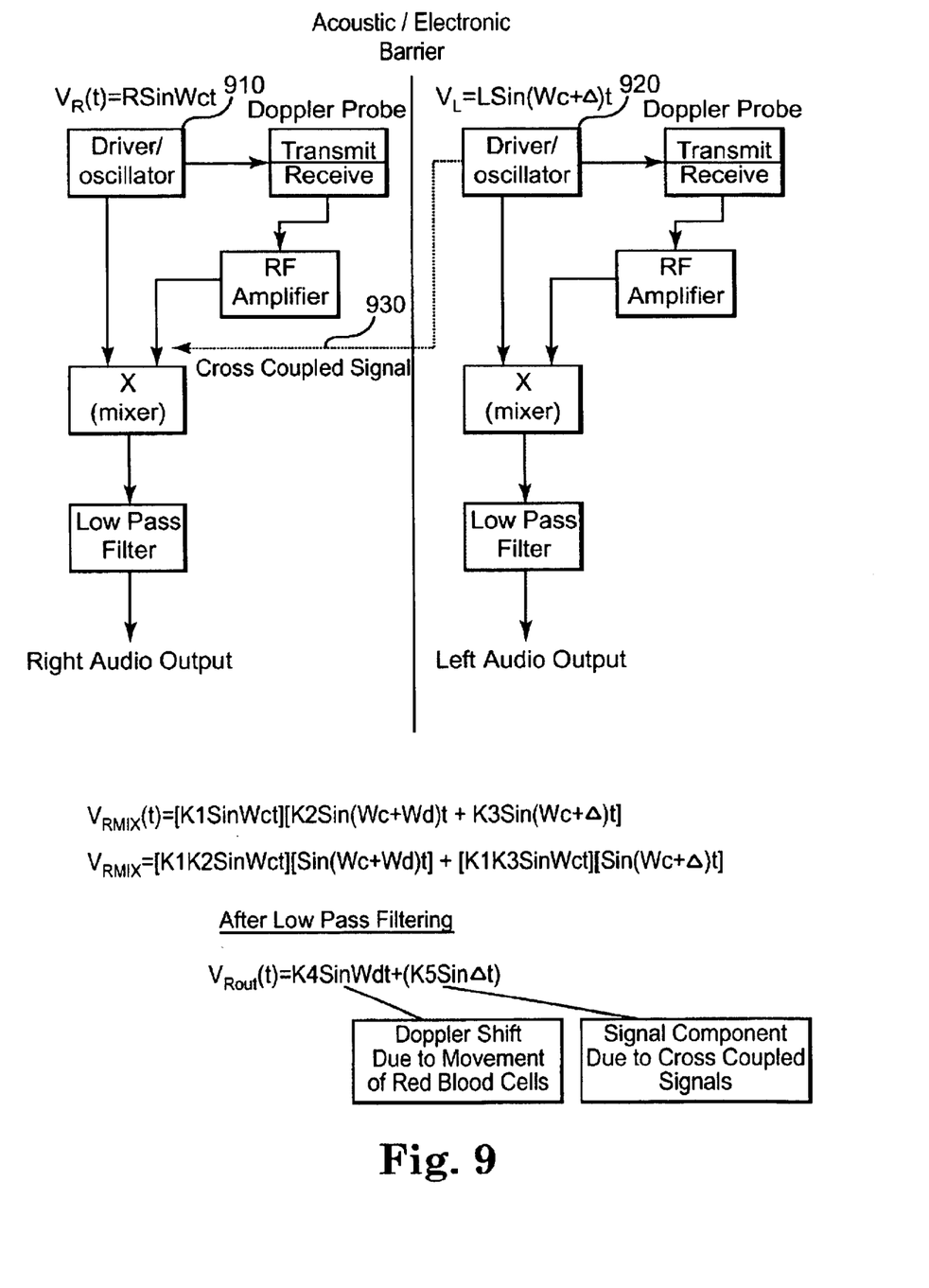
FIG. 9 schematically shows a convention arrangement for simultaneous blood flow measurement.

However, simultaneous bilateral Doppler measurements have not been successfully used in conventional systems and techniques. One conventional approach is to employ two separate Doppler circuits operating at nominally the same frequency, e.g., 8 MHz. Such approach suffers from at least two drawbacks. First, it is difficult to maintain an exact frequency match between the two circuits; second, as schematically illustrated in FIG. 9, even if the drivers 910, 920 of the two Doppler circuits could be matched exactly, or even if the two drivers were in fact a common driver, the signals in both circuits are like to cross-couple (930) with each other, both electronically and acoustically due to the nearly-identical frequencies of the signals. The magnitude of the error signals resulting from such interference is in the same bandwidth, and can be on the same order of magnitude or even greater than, the useful signals. Driving two transducers from a common signal driver to eliminate frequency drift does not solve the cross coupling problem as the return Doppler signals can cross couple in the same way as heretofore described.

The invention disclosed herein is aimed at providing a system and method for simultaneous, bilateral measurement of segmental blood pressures substantially without the drawbacks of the conventional approaches.

SUMMARY OF THE INVENTION

Generally, the invention provides a system and method whereby two Doppler measurements of blood flow at two different locations on a body are carried out substantially simultaneously, i.e., within the same heartbeat with minimum interference from each other.

In one illustrative embodiment of the invention, two Doppler modules are configured to operate at nominally the same Doppler carrier frequency so that they probe for substantially the same range of physiological information. However, the Doppler carrier frequencies for the Doppler modules are also sufficiently different to substantially avoid interference between the two modules. A phase-locked loop (PLL) used to demodulate the velocity signals in each Doppler module efficiently blocks interference signals because they have frequencies that are the difference in the Doppler carrier frequencies and that are outside the locking range of the PLL. Broad-band RF amplifiers and Doppler transducers are used to ensure that the frequency responses of the Doppler modules are substantially the same.

BRIEF DESCRIPTION OF THE DRAWINGS

Other objects and advantages of the invention will become apparent upon reading the following detailed description and upon reference to the drawings in which:

FIG. 2(*a*) schematically shows a double-tuned RF amplifier used in a Doppler module in an embodiment of the invention;

FIG. 2(*b*) schematically shows the frequency response characteristics of the amplifier shown in FIG. 2(*a*);

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Generally according to the invention, a system and method for simultaneous (i.e., within the same heartbeat) blood flow measurements at two or more locations on a patient's body are provided. The system in one embodiment includes one Doppler module for taking measurements from each location. All Doppler modules are tuned to nominally the same frequency (e.g., 8 MHz) but each is tuned to a slightly different Doppler carrier frequency (e.g., 7.8 MHz) from the others. The difference is sufficiently large so that the interference between the modules is sufficiently small in the output frequency range of interest.

Figure 1:
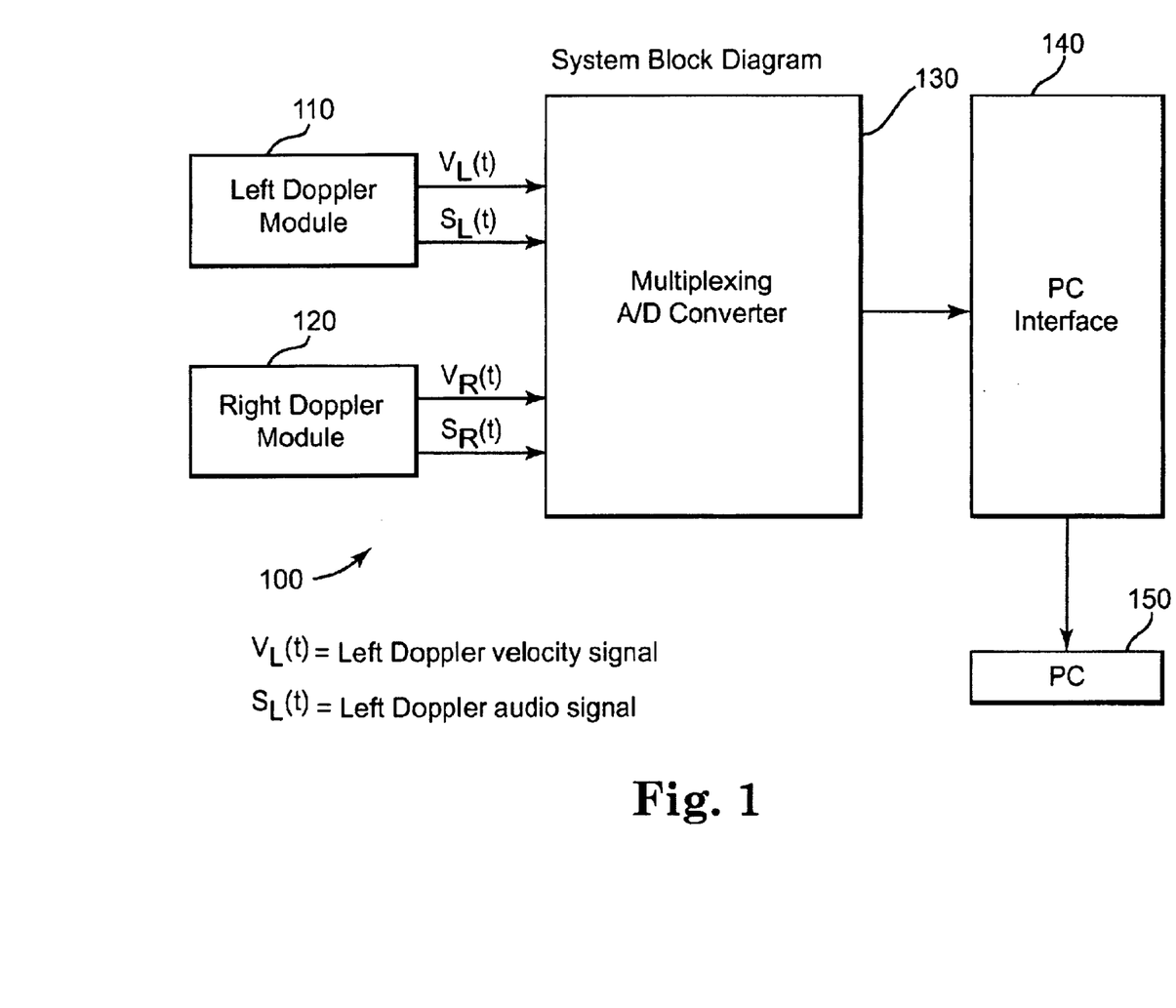
FIG. 1 schematically shows an over-all system for simultaneous segmental sphygmomanometry in one embodiment of the invention.

An over-all system 100 embodying the invention is schematically illustrated in FIG. 1. Two Doppler modules are used. The left Doppler module 110 is configured to launch ultrasonic signals into one side of a patient's body and generate from the ultrasonic signals received back from the body two signals: (1) a left Doppler velocity signal, $V_L(t)$, which is indicative of the speed of blood flow; and (2) a left Doppler audio signal, $S_L(t)$, the frequency of which is the difference in frequency between the ultrasonic signal launched into the patient and the response signal received by the module 110. The right Doppler module 120 is identically constructed as the left Doppler module 110 but is intended to be place on the other side of the patient's body to generate a right Doppler velocity signal, $V_R(t)$ and a right Doppler audio signal, $S_R(t)$. Although velocity and audio signals are used in this illustrative embodiment to enhance the reliability and ease of use of the system, it is not necessary to have both types of signals. However, typically audio signals are used at least to aid the location of blood vessels. The two modules 110, 120 are tuned to different Doppler carrier frequencies, as described in more detailed below.

The Doppler modules 110 and 120 are tuned nominally at the same carrier frequencies. For example, for shallow vessel studies, the modules can be tuned to around 8 MHz. However, they are deliberately tuned to carrier frequencies that differ from each other by an amount that results in minimized interference in the desired signals produced by the modules 110, 120. The carrier frequency difference is typically at least the greatest of (a) the maximum frequency of human hearing, if audio signals are used, (b) the maximum Doppler difference frequency expected to be found due to hemodynamic flow, and (c) the bandwidth of the demodulator (such as the lock range of the PLL; see below) in the Doppler module. Thus, for example, for a maximum human hearing range of 25 kHz, maximum expected Doppler shift of 15 kHz and PLL lock range of 10 kHz, the carrier frequency difference should typically be at least 25 kHz. A safer choice would be to have a carrier frequency difference of at least the sum of the three factors above. For the above numerical example, the difference would be about 50 kHz. Further enhancement of signal quality can be achieved by choosing an even greater frequency difference, such as 100 kHz or 200 kHz.

For example, one of the modules can be tuned to 8 MHz and the other 8.2 MHz. For the same blood flow conditions, the two modules do not produce perceptibly different Doppler audio or velocity signals. But the 200 kHz frequency difference ensures that any interference between the two modules will have a frequency of 200 kHz, which is sufficiently distant from all frequencies of the desired signals and thus easily filtered. The 200 kHz frequency is also outside the lock range of the phase-locked loop 492 (see below) and audio range. The interference noise is therefore minimized.

The signals produced by the Doppler modules 110, 120 are sent to a Multiplexing analog-to-digital (A/D) converter 130 to be digitized for later computer processing. The precise method and order of multiplexing and conversion is not critical to the invention. Any number of alternative devices and methods can be used in place of the converter 130. For example, the signals need not be multiplexed, but instead sent in parallel for subsequent computer processing. A computer interface (140), such as a digital I/O board receives the digitized signals and transfer them to a computer 150, which in the illustrative embodiment is a personal computer (PC) but can be any suitable computer or processor. The computer 150 is programmed to perform from the basic functions such as calculating and displaying blood pressures from the various signals to automating signal detection, as described later.

Figure 2:
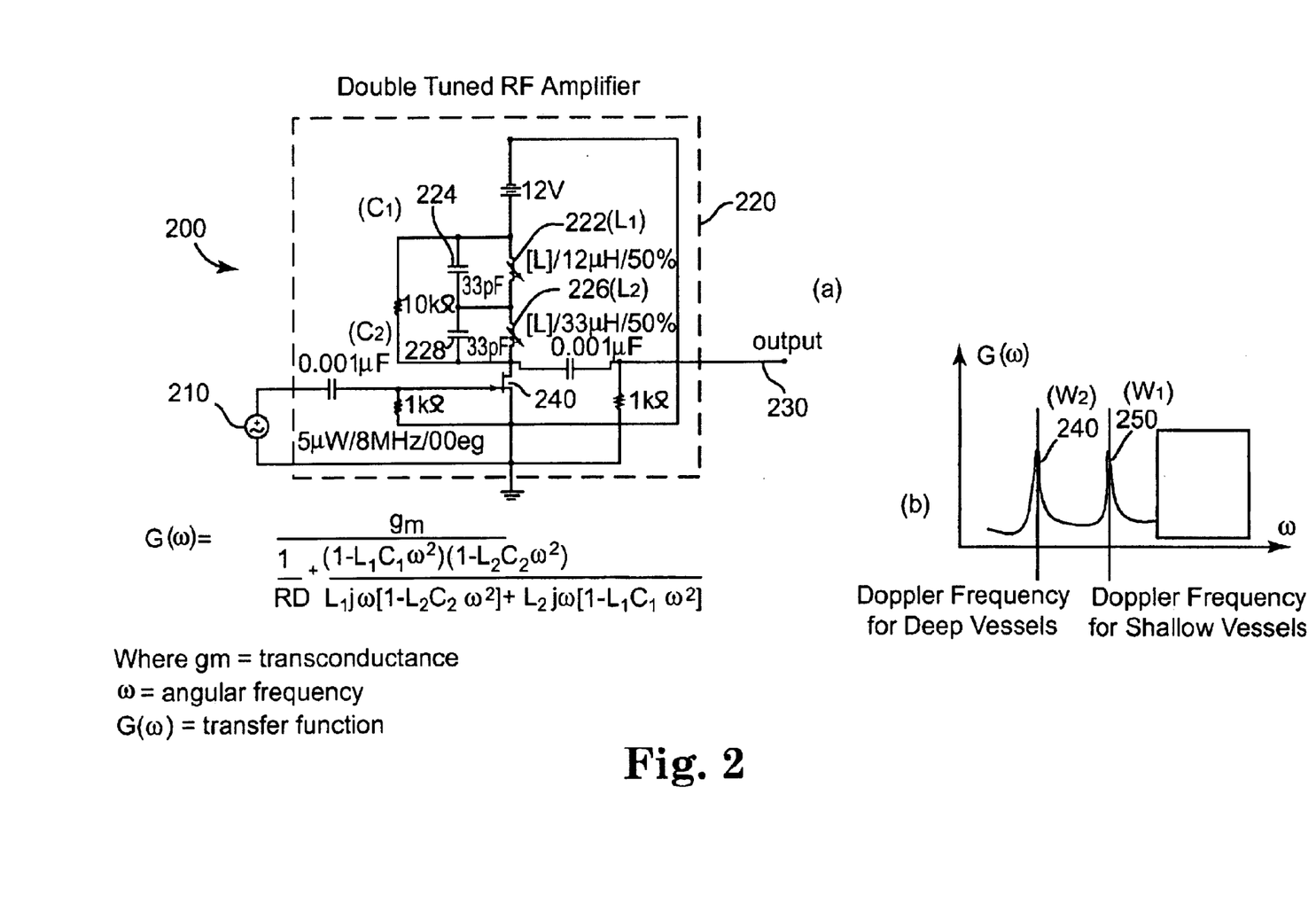
Figure 4:
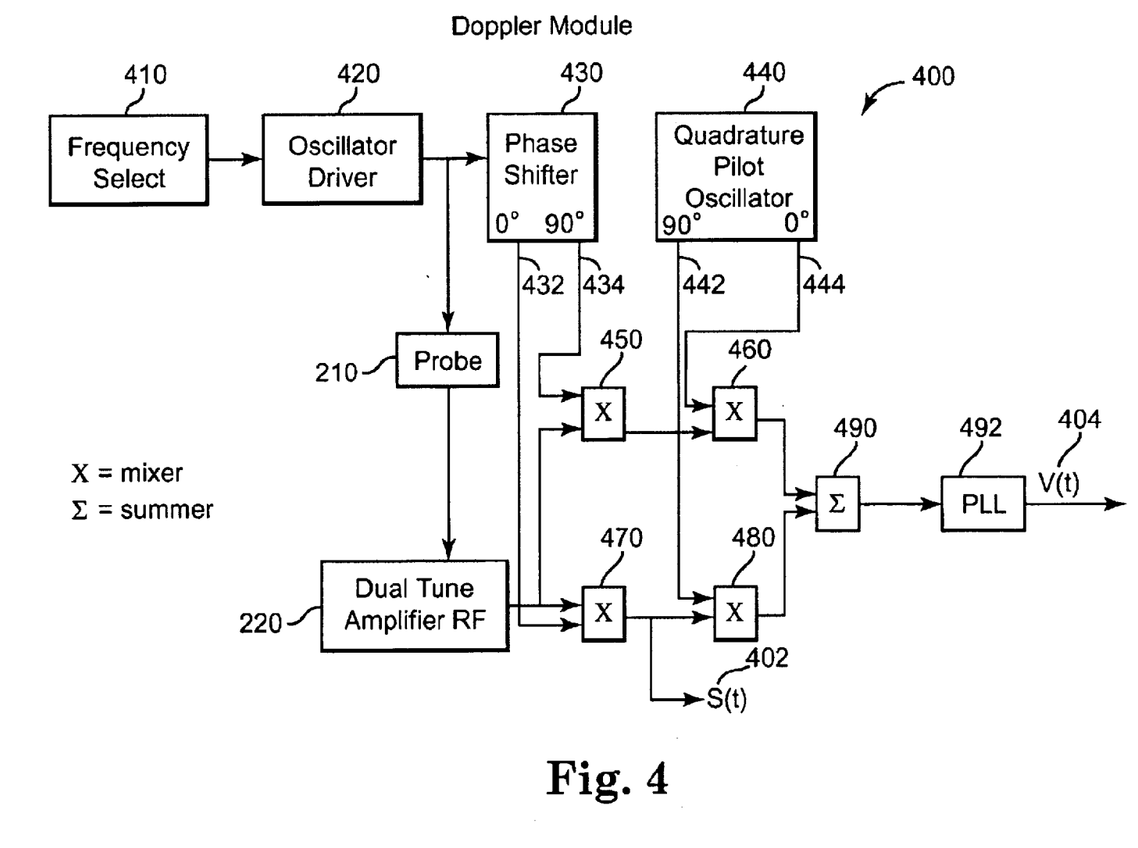
FIG. 4 shows in block-diagram form the structure of a Doppler Module in an embodiment of the invention.

Each of the Doppler modules 110, 120, as schematically shown in FIG. 4 (labeled 400) includes a probe or transducer module 210, which is driven by an oscillator driver 420, the frequency of which is in turn controlled by a frequency selector 410. The transducer module 210 can launch ultrasonic signals into a patient body and receive echoes back. The echoes, which are ultrasonic signals, are converted into radio-frequency (RF) signals by the transducer module 210, which then sends the RF signals to an RF amplifier 220. The amplifier 220 can be any suitable amplifier for the signals, but in the illustrative embodiment of the invention is a "double-tuned" RF amplifier, as schematically shown in FIG. 2(a). Signals from the transducer module 210 is fed to the amplifier 220, which includes an RF transistor 240 and two inductor-capacitor pairs $L_1$ (222)-$C_1$ (224) and $L_2$ (226)-$C_2$ (228). Each pair results in a resonance frequency in the amplifier's frequency response. Thus the amplifier is tuned to two frequencies (channels) by adjusting the values of the appropriate inductors or capacitors. In the illustrative embodiment, the amplifier is tuned to 8 MHz and 5 MHz, respectively. The former Doppler frequency is better suited for studying shallow vessels while the latter more suited for deep vessels. Again, the bandwidth of each channel is narrow enough to reject unwanted interference but large enough (e.g., about 200 kHz) to be suitable for a range of Doppler carrier frequencies The transducers module 210 used are wide-band ultrasonic transducers to ensure that the frequency response is substantially the same no matter what carrier frequency a Doppler module is tuned to with in the specified range. For example, the bandwidth in an illustrative embodiment is chosen to be large enough to encompass the carrier frequencies for both shallow and deep vessels and the range of possible frequency settings for each nominal frequency, as discussed above. Thus, for the example above of the RF amplifier tuned to 8 and 5 MHz, the transducers have bandwidths of about 3 MHz or larger, for example 4 MHz.

Figure 3:
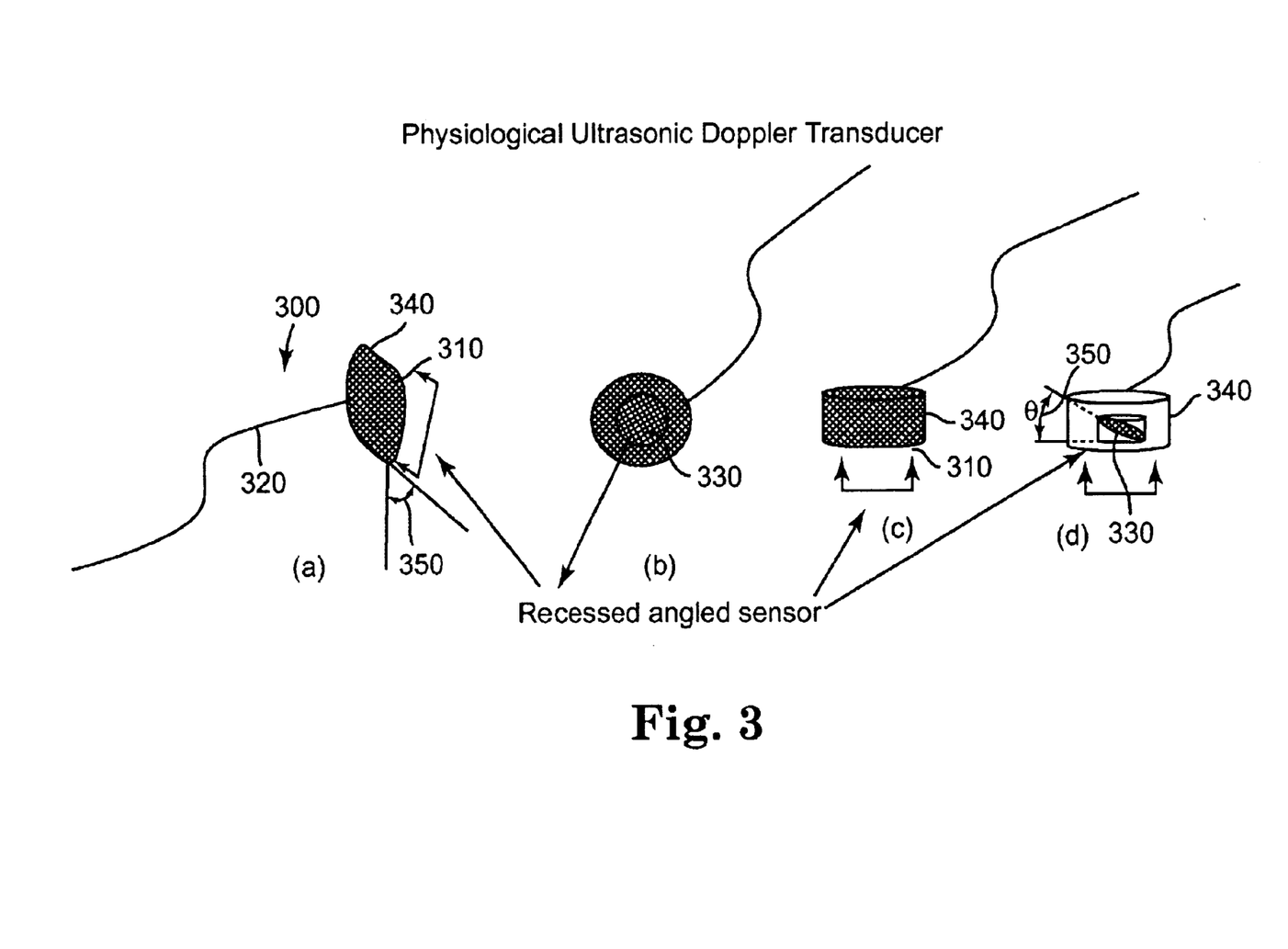
FIG. 3 schematically shows various aspects of a Doppler transducer module in an embodiment of the invention.

The transducer modules can also be physically configured for convenient application and minimizing motion artifact. In one embodiment of the invention, as shown in FIGS. 3(a) and 3(b), a transducer module 300 includes leads 320, housing 340 and transducer 330 connected to the leads and situated within the housing. The transducer 330 is typically positioned inside the housing 340 in such a way that when the housing is attached to a patient in the intended manner, the transducer is oriented with a component of the orientation vector parallel to the blood flow in the target blood vessel. The housing 340 is a slanted section of a circular cylinder, with the plane defined by a patient-contacting end 310 not being perpendicular to the longitudinal axis of the cylinder. The transducer 330, in contrast, is positioned perpendicular to the longitudinal axis of the cylinder. Thus, when the transducer module 300 is properly positioned on a patient with the patient-contacting end in contact with a portion of the patient's skin, the transducer is at an angle from, and not parallel or perpendicular to the portion of the skin. For example, an angle of 40 to 60 degrees. A similar arrangement is show in FIGS. 3(c) and 3(d), where the housing 340 is shown as a right circular cylinder but with the transducer 330 positioned at an angle from the longitudinal axis of the cylinder.

Figure 6:
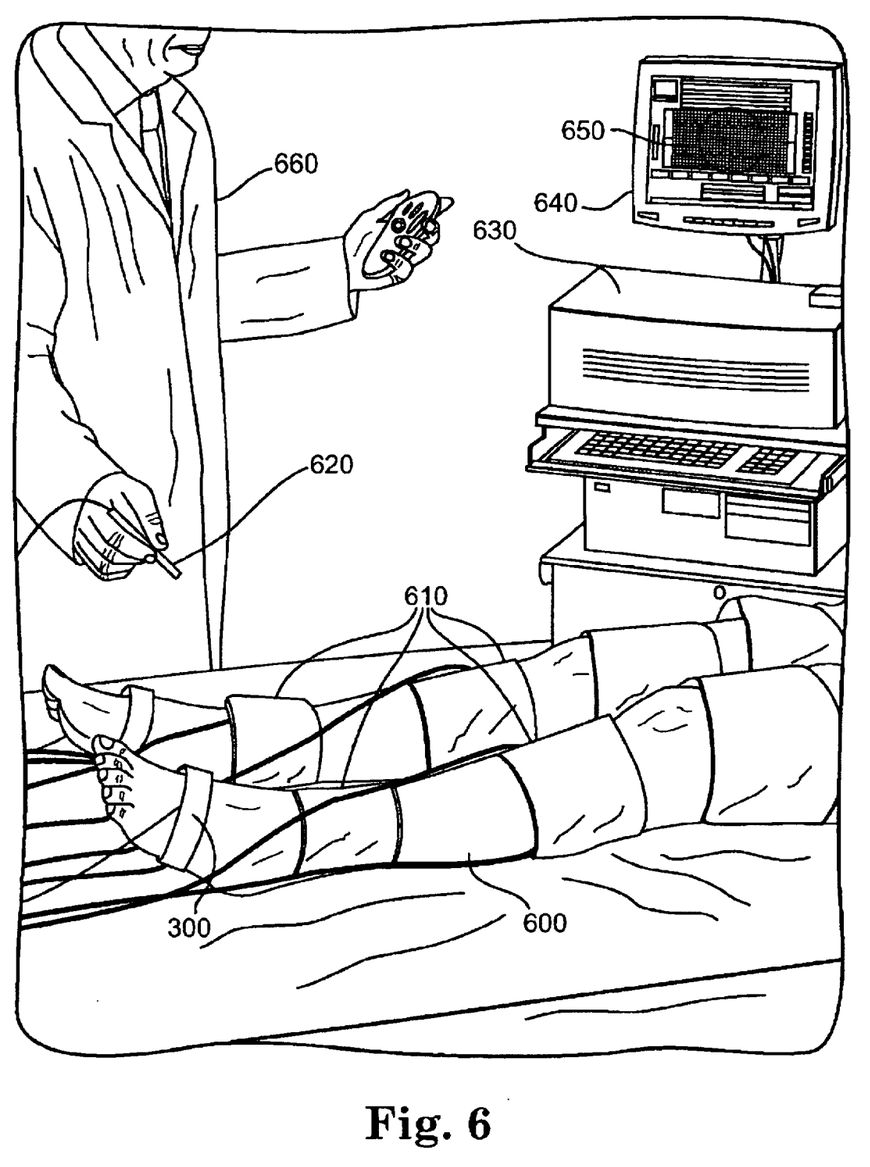
FIG. 6 schematically shows an arrangement for simultaneous segmental sphygmomanometry in one embodiment of the invention.

In both examples, the transducer modules are "flat", i.e., the height of the modules 330 (the dimension perpendicular to the patient-contacting end) is smaller or at least not substantially larger than the dimensions of the patient-contacting end. This configuration allows the transducer modules to be easily and securely fastened to a patient, as shown in FIG. 6. Motion artifacts are therefore greatly reduced.

Figure 5:
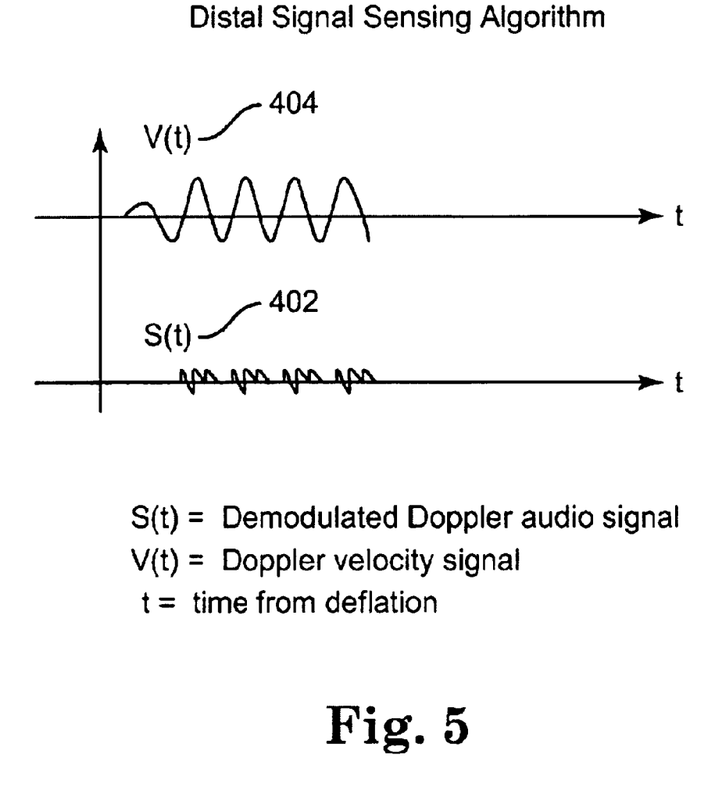
FIG. 5 schematically shows the forms of a Doppler velocity signal and Demodulated Doppler audio signal output from a Doppler module in an embodiment of the invention.

Referring again to FIG. 4, the amplified RF signal from the transducer module 210 is mixed by mixer 470 with the original signal from the oscillator driver 420 through a phase shifter 430 but without any phase shift. The result of the mixing is an audio signal S(t), with a frequency of the difference between the inputs to the mixer 470. The amplified signal is also mixed by mixer 450 with a 90-degree-shifted oscillator driver signal. The resultant signal is mixed by mixer 460 with a signal generated by a quadrature pilot oscillator 440, which is an oscillator having two outputs that are of the same frequency but shifted 90° from each other. The frequency of the oscillator 440 can be chosen at any value that is at least the maximum Doppler shift in magnitude away from the baseband. For blood pressure measurements, it is typically at least 100 kHz and well away from the Doppler carrier frequencies. The audio signal S(t) is mixed by mixer 480 with a 90-degree-shifted signal generated by the quadrature pilot oscillator 440. The outputs of mixers 460 and 480 are combined by a summer 490 to produce an intermediate-frequency signal, which is in turn demodulated by a phase-locked loop (PLL) 492 to produce a Doppler velocity signal, V(t), which has an amplitude that is proportional to the speed of the detected blood flow, as shown in FIG. 5 (404).

Figure 8:
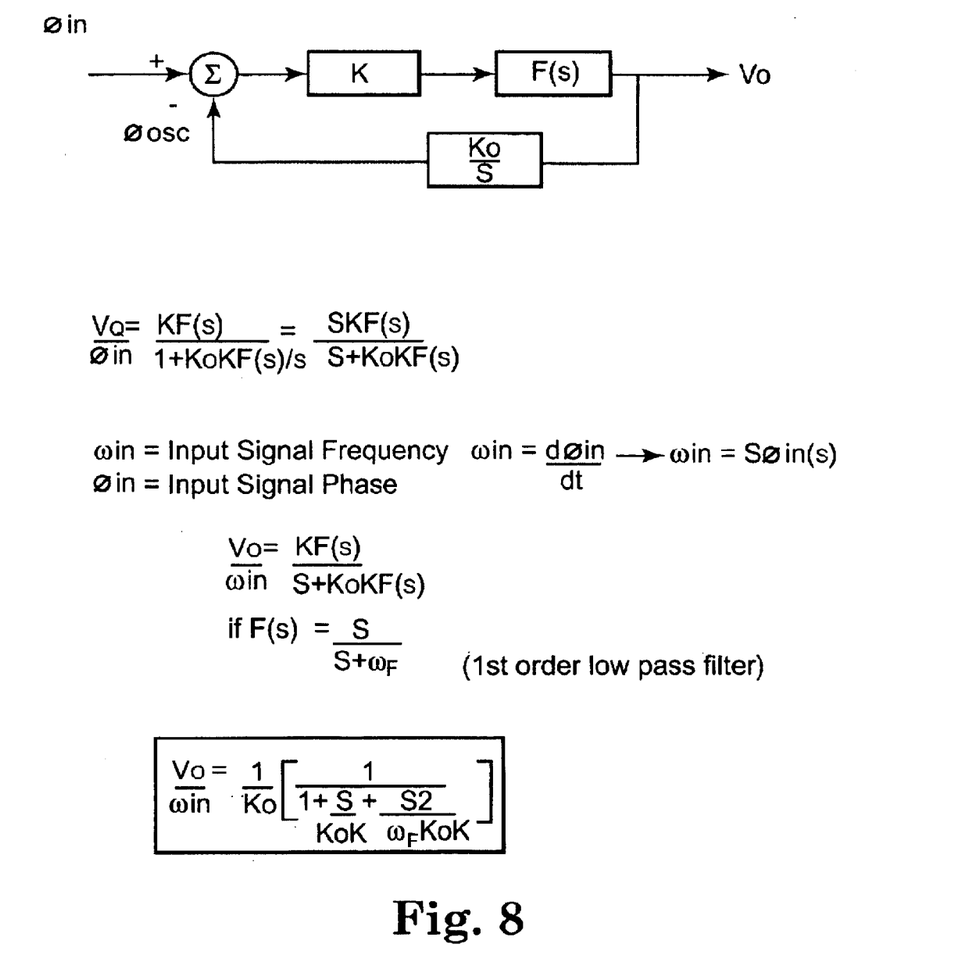
FIG. 8 schematically shows a phase-locked loop used in a Doppler module in an embodiment of the invention.

The PLL, an example of which is shown in FIG. 8, is a device well known in the art and provides several advantages over other alternative devices and methods for demodulation. First, it allows for small amplitude frequency components to contribute to the time domain output. Second, it can selectively sense small signals over noise. Third, it generally rejects small amplitude, out-of-band signals that might typically trigger other types of demodulators, such as a zero crossing detector. Fourth, it rejects signals with frequencies beyond the lock range, thus ensuring that a Doppler module does not interfere with another Doppler module on the contra-lateral side.

A further illustrative embodiment of the invention is schematically shown in FIG. 6. Pairs of inflatable cuffs 610 are wrapped around a patient (600)'s respective legs and feet. Each cuff 610 is equipped with a calibrated pressure sensor (not shown) for measuring the air pressure in the cuff (610). A disk-shaped Doppler sensor 300 is secured against the patient's skin and oriented to measure blood pressures from a set of predetermined arteries. A pen-style Doppler transducer 620 is readily accessible to the physician or technologist 660 carrying out the measurements. Each transducer 300, 620 is attached to its corresponding Doppler module. Alternatively, the pairs of transducers 300 at different segments (feet, ankles, calves, etc.) are connected time-wise sequentially to the same pair of Doppler modules through a set of switches, which can be manually or electronically operated. The Doppler modules 300, 620 can be controlled by a computer, such as a PC 630, which also includes a display 640 for monitoring (650) the measurements. The inflation and deflation of the cuffs and cuff pressure monitoring can also be computer controlled.

Figure 7:
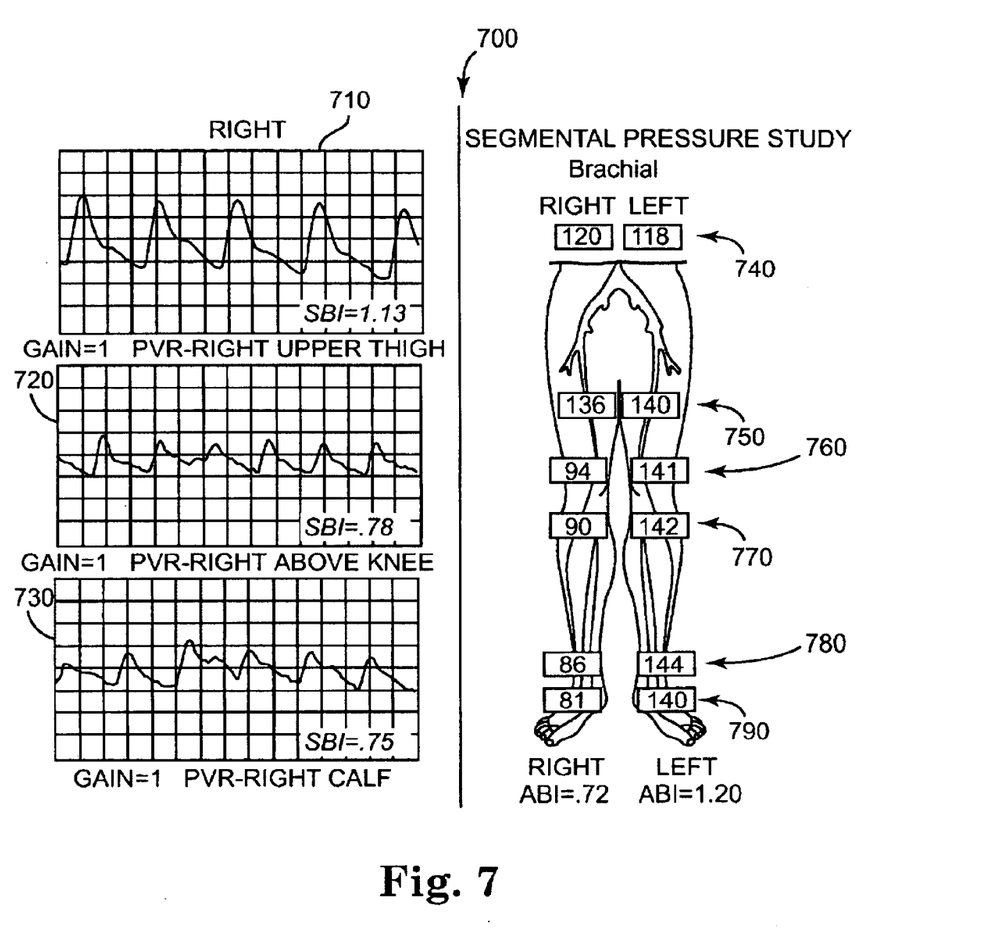
FIG. 7 schematically shows a sample result of simultaneous segmental sphygmomanometry accompanied by the result of PVR measurements in one embodiment of the invention.

In operation, each pair of Doppler modules 300 operate at slightly different frequencies from each other as described above. For measurements in each section, the corresponding cuffs 610 securing the transducers 300 in the section are first inflated until the blood flow through the arteries in the section is stopped. At this point, because there is no blood speed in the section, both the Doppler velocity signal and Doppler audio signal are zero. As the cuff pressure is gradually decreased, at some cuff pressure, blood flow resumes, and Doppler audio and velocity signals are again detected, as schematically shown in FIG. 5. The cuff pressure measured at the onset of resumption of the Doppler signals is the systolic blood pressure. If the blood flow resumes sooner on one side than it does on the other, the patient has different segmental blood pressure on different sides. Drastically asymmetrical segmental blood pressures, as in the example shown in FIG. 7 (740–790), may indicate vascular ailment. The segmental pressure results can further be compared with results from using other techniques, such as pulse volume recording (PVR) for the same regions to gain further insight, as shown in FIG. 7, which shows markedly blunted PVR wave forms for the right leg in the same regions where the Doppler segmental pressures are asymmetrical.

According to another aspect of the invention, the computer 150, which in an illustrative embodiment is a PC, can be programmed to increase the efficiency and reliability of blood pressure measurements. For example, an algorithm is utilized to enhance signal discrimination in the following illustrative way.

Both the Doppler audio signals and Doppler velocity signals are sampled during the cuff inflation and deflation processes and temporarily stored in memory. The computer 150 continuously examines the signals to see if a particular threshold amplitude for each type of signals is exceeded. If both types of signals have exceeded their respective thresholds a set number of (e.g., three) consecutive times in the same time frame, then the first detected signals that exceeded their respective thresholds are deemed valid.

As another example, the PC 150 can be programmed to automatically determine if a signal has reached a threshold level. For example, a threshold level can be set at a predetermined gradation (e.g., first gradation) on the graphic display 640. Increasing the gain of displayed signal ("zooming in") therefore has the effect of lowering the threshold, and decreasing the gain has the opposite effect. Thus, a user can adjust the threshold to a level most suitable for his or her particular application.

Thus, the invention enables simultaneous, bilateral segmental blood pressure measurement using the ultrasonic Doppler method, which is the method of choice for studying vascular diseases. Unlike other techniques, the invention provides both waveforms as output (velocity signals) as well as audio signals. Photoplethymography, for example, only provides waveforms outputs. In addition, simultaneous bilateral testing significantly reduces testing time while maintaining, or enhancing the quality of testing.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A system for simultaneously measuring blood pressures at least two locations on a body, the system comprising:
   (a) a first Doppler module tuned to a first Doppler carrier frequency and configured to obtain a first signal from one of the two locations, the first signal being indicative of a parameter of blood flow at the first location; and
   (b) a second Doppler module tuned to a second Doppler carrier frequency, which is higher than the first Doppler carrier frequency by at least about 25 kHz and configured to obtain a second signal from the other one of the two locations, the second signal being indicative of a parameter of blood flow at the second location, the two Doppler modules being configured to obtain the respective signals substantially simultaneously.

2. The system of claim 1, wherein the second Doppler carrier frequency is further higher than the first Doppler carrier frequency by at least about 100 kHz.

3. The system of claim 1, wherein each Doppler module has a Doppler velocity signal output port with an output bandwidth, and the second Doppler carrier frequency is higher than the first Doppler carrier frequency by an amount greater than the output bandwidth.

4. The system of claim 3, wherein each Doppler module further includes a phase-locked loop operatively connected to the output port and configured to transmit the Doppler velocity signal to the output port, the phase-locked loop having a lock range, wherein the difference between the second and first Doppler carrier frequencies is greater than the lock range.

5. The system of claim 3, wherein each Doppler module further includes a Doppler transducer configured to receive ultrasonic signals from a body and convert the signals into radio-frequency electrical signals, and a radio-frequency amplifier operatively connected to the transducer.

6. The system of claim 5, wherein the transducer in each Doppler module has a bandwidth of about 3 MHz.

7. The system of claim 5, wherein the transducer in each Doppler module has a bandwidth of about 4 MHz.

8. The system of claim 5, wherein each Doppler module further includes a transducer housing having a patient-contacting end configured to contact a patient's skin over an area, the transducer being oriented within the transducer housing such that when the patient-contact area of the housing is placed in contact with a patient's skin over an area, the transducer is inclined with respect to the skin area at an angle between about 40 to about 60 degrees.

9. The system of claim 8, wherein the transducer housing defines a height that is smaller than a dimension of the patient-contact area.

10. The system of claim 5, wherein the amplifier has a passband having a bandwidth of at least about 1 MHz.

11. The system of claim 5, wherein the amplifier has passband having an adjustable center frequency.

12. The system of claim 10, wherein the amplifier is tuned to at least a first frequency for measuring blood pressure of deep vessels and a second frequency for measuring blood pressure of shallow vessels.

13. The system of claim 5, wherein each Doppler module further includes an audio output configured to transmit signal indicative of the frequency difference between a signal launched into the body and a signal received from the body in response.

14. A system for simultaneously measuring blood pressures at least two locations on a body, the system comprising:
   (a) a first Doppler module tuned to a first Doppler carrier frequency and configured to obtain a first signal from one of the two locations, the first signal being indicative of a parameter of blood flow at the first location; and
   (b) a second Doppler module tuned to a second Doppler carrier frequency, which is higher than the first Doppler carrier frequency by at least the greater of the maximum frequency of human hearing and a maximum Doppler frequency expected due to hemodynamic flow, and configured to obtain a second signal from the other one of the two locations, the second signal being indicative of a parameter of blood flow at the second location, the two Doppler modules being configured to obtain the respective signals substantially simultaneously.

15. The system of claim 14, wherein each Doppler module further includes a demodulator having a bandwidth and configured to generate a signal indicative of the speed of the blood flow, and the second Doppler carrier frequency is higher than the first Doppler carrier frequency by at least the greatest of (a) the maximum frequency of human hearing, (b) a maximum Doppler frequency expected due to hemodynamic flow and (c) a bandwidth of the demodulator.

16. The system of claim 15, wherein the demodulator includes a phase-locked loop having a lock range, the second Doppler carrier frequency is higher than the first Doppler carrier frequency by at least the greatest of (a) the maximum frequency of human hearing, (b) a maximum Doppler frequency expected due to hemodynamic flow and (c) the lock range of the phase-locked loop.

17. A method of measuring blood pressure in a body, the method comprising:
   (a) launching a first ultrasonic signal of a first Doppler carrier frequency into a first location of the body;
   (b) receiving a first response signal from the first location, the first response signal being indicative of a parameter of blood flow at the first location;
   (c) substantially simultaneously with step (a), launching a second ultrasonic signal of a second Doppler carrier frequency into a second location of the body, the second Doppler carrier frequency being higher than the first Doppler carrier frequency by at least about 25 kHz; and
   (d) receiving a second response signal from the second location, the second signal being indicative of a parameter of blood flow at the second location.

18. The method of claim 17, further comprising comparing the first and second response signals.

19. The method of claim 17, further comprising:
   (e) applying a sufficient first pressure at the first location to stop blood flow in a blood vessel in the first location;

(f) applying a sufficient second pressure at the second location to stop blood flow in a blood vessel in the second location;

(g) after steps (e) and (f), reducing while monitoring the first and second pressures until the blood flows in both blood vessels are restored; and (h) repeating steps (a) through (d) throughout step (g); and (i) determining, from the signals received in steps (b) and (d), the levels of the first and second pressures at which the blood flows in the blood vessels in the first and second locations, respectively, are restored.

20. The method of claim 17, further comprising:

(e) generating a first output signal derived from the first ultrasonic signal and the first respond signal; and (f) generating a second output signal derived from the second ultrasonic signal and the second respond signal.

21. The method of claim 20, wherein the parameter of blood flow at each location is the speed of blood flow at that location, and each output signal is an audio signal having a frequency proportional to the speed of blood flow at the respective location.

22. The method of claim 20, wherein the parameter of blood flow at each location is the speed of blood flow at that location, and each output signal has amplitude proportional to the speed of blood flow at the respective location.

23. The method of claim 17, wherein the second Doppler carrier frequency is higher than the first Doppler carrier frequency by at least the greater of the maximum frequency of human hearing and a maximum Doppler frequency expected due to hemodynamic flow.

24. The method of claim 23, wherein the step of receiving a first response signal includes demodulating the first response signal using a first demodulator, and the step of receiving a second response signal includes demodulating the second response signal using a second demodulator, each of the modulators having a bandwidth, and the second Doppler carrier frequency is higher than the first Doppler carrier frequency by at least the greatest of (a) the maximum frequency of human hearing, (b) a maximum Doppler frequency expected due to hemodynamic flow and (c) a bandwidth of the demodulator.

* * * * *